US007076293B2

(12) United States Patent
Wang

(10) Patent No.: US 7,076,293 B2
(45) Date of Patent: Jul. 11, 2006

(54) COMPUTER-AIDED AUTOMATIC VITAL ACUPUNCTURE POINT ALIGNMENT AND ELECTRONIC ACUPUNCTURE METHOD AND A SYSTEM TO PERFORM THE METHOD

(75) Inventor: Wei-Cheng Wang, 4th Fl., No. 43, Tzu Chiang Hsin Tsun, Panchiao City, Taipei Hsien (TW)

(73) Assignee: Wei-Cheng Wang, Taipei Hsien (TW)

( * ) Notice: Subject to any disclaimer, the term of this patent is extended or adjusted under 35 U.S.C. 154(b) by 477 days.

(21) Appl. No.: 10/653,272

(22) Filed: Sep. 3, 2003

(65) Prior Publication Data

US 2004/0111128 A1 Jun. 10, 2004

(30) Foreign Application Priority Data

Dec. 6, 2002 (EP) ................................ 02258438

(51) Int. Cl.
*A61N 1/00* (2006.01)

(52) U.S. Cl. .......................... 607/2; 600/300; 128/907; 607/46

(58) Field of Classification Search ................ 128/907; 606/189; 600/300; 607/2, 46
See application file for complete search history.

(56) References Cited

U.S. PATENT DOCUMENTS 5,366,379 A * 11/1994 Yang et al. ................. 434/365
5,779,483 A * 7/1998 Cho ........................... 434/262

FOREIGN PATENT DOCUMENTS

JP 2002078772 A * 3/2002

* cited by examiner

*Primary Examiner*—Robert E. Pezzuto
*Assistant Examiner*—Joy Patel
(74) *Attorney, Agent, or Firm*—Troxell Law Office, PLLC

(57) ABSTRACT

A computer-aided automatic vital acupuncture point alignment and electronic acupuncture method uses a system comprised of a computer, a digital imaging device, a digital probe device and an electronic acupuncture device. The computer takes a picture of a patient's body with the digital imaging device and automatically marks vital acupuncture points on the picture from a standard body's picture on which all vital acupuncture points are marked and localizes the vital acupuncture points on the patient's skin with the digital probe device. A practitioner uses the electronic acupuncture device to touch the vital acupuncture points on the patient's skin based on the patient's picture. The computer outputs a suitable wave signal through the electronic acupuncture device to the skin. Therefore, the present invention identifies the vital acupuncture points on the skin to have a good curative effect.

7 Claims, 3 Drawing Sheets

COMPUTER-AIDED AUTOMATIC VITAL ACUPUNCTURE POINT ALIGNMENT AND ELECTRONIC ACUPUNCTURE METHOD AND A SYSTEM TO PERFORM THE METHOD

BACKGROUND OF THE INVENTION

1. Field of the Invention

The present invention relates to a computer-aided automatic vital acupuncture point alignment, electronic acupuncture method and a system to perform the method, and more particularly to an electronic acupuncture method with a capability of accurately aligning with vital acupuncture points for a good curative effect.

2. Description of Related Art

Chinese people believe that vital acupuncture points of the body can be stimulated to soothe or relieve discomfort. In the past, Chinese practitioners inserted needles into positions in the body where vital acupuncture points were located to stimulate the vital acupuncture points. Recently, electronic acupuncture devices have been developed to provide safer and more convenient treatment than traditional acupuncture needles.

The electronic acupuncture devices stimulate a vital acupuncture point of the body with a fixed frequency electric signal. Although the fixed frequency electric signal stimulates the vital acupuncture point, vital acupuncture points become desensitized to the electric current over time so that the effect of healing is decreased after repeated treatments. Eventually, when the vital acupuncture points become desensitized to the electric current, the treatment will not relieve the patient's discomfort. Therefore, one electronic stimulative acupuncture device outputs a variable wave signal to stimulate the vital acupuncture point more effectively than the previous electronic acupuncture device. However, practitioners using the electronic stimulative acupuncture device often directly touch the skin in a position that causes further discomfort rather than the desired vital acupuncture points. Thus, this electronic stimulative acupuncture device does not always have a good curative effect.

To overcome these shortcomings, the present invention provides an improved computer-aided electronic acupuncture device to locate and to stimulate vital acupuncture points to mitigate or obviate the aforementioned problems.

SUMMARY OF THE INVENTION

The primary objective of the present invention is to provide accurate vital acupuncture point alignment of an acupuncture device for good acupuncture treatment for a patient.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
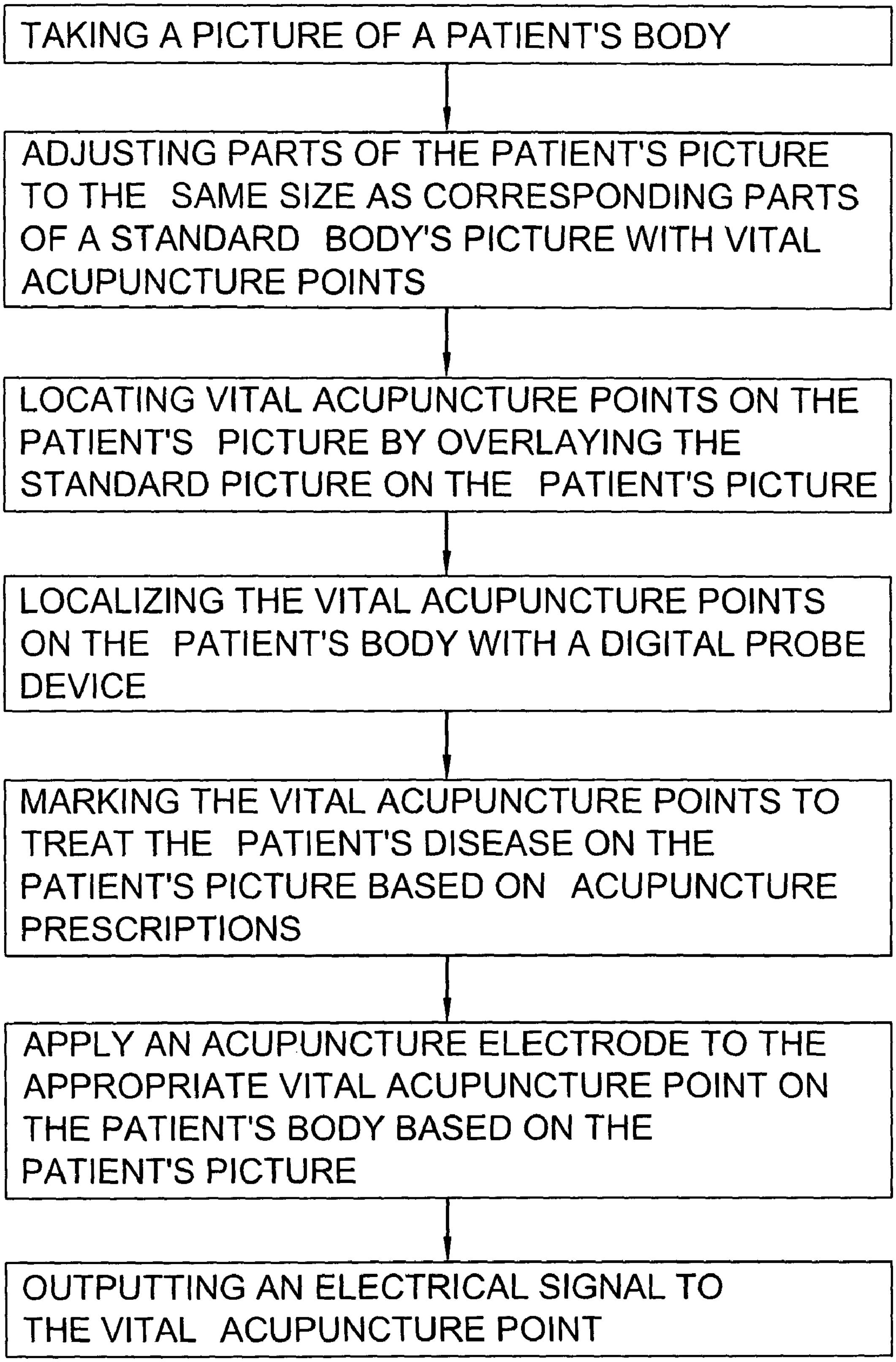
FIG. 1 is a flow chart of a vital acupuncture point alignment and electronic acupuncture method in accordance with the present invention.

With reference to FIG. 1, a method to perform electronic acupuncture includes the steps of (a) taking a picture of a patient's body; (b) adjusting parts of the patient's picture to the same size as corresponding parts of a standard body's picture with vital acupuncture points; (c) locating vital acupuncture points on the patient's picture by overlaying the standard picture on the patient's picture; (d) localizing the vital acupuncture points on the patient's body with a digital probe device; (e) marking the vital acupuncture points to treat the patient's disease on the patient's picture based on acupuncture prescriptions; (f) apply an acupuncture electrode to the appropriate vital acupuncture point on the patient's body based on the patient's picture; and (g) outputting an electrical signal to the vital acupuncture point.

Figure 2:
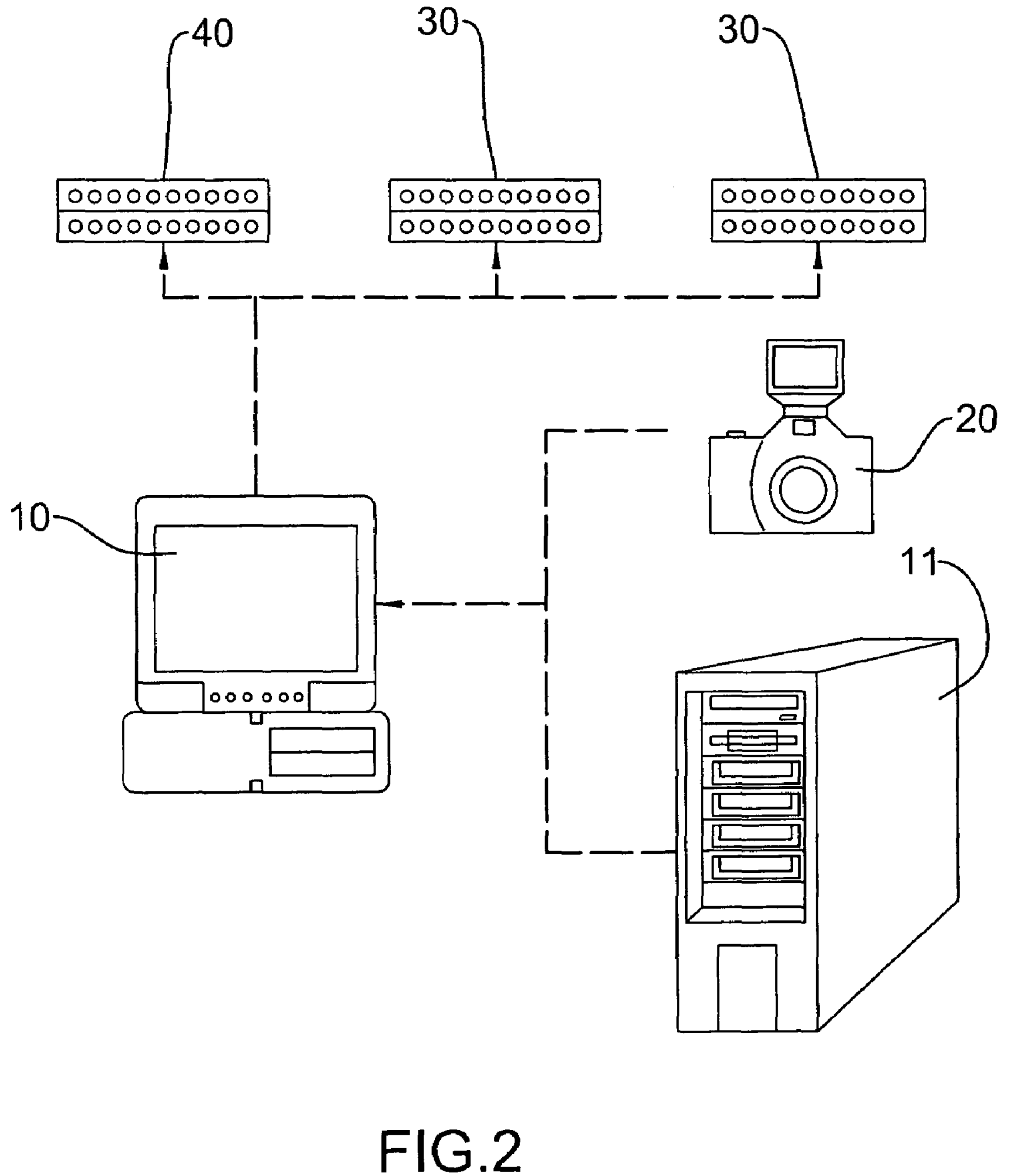
FIG. 2 is a schematic diagram of a computer-aided electronic acupuncture device in accordance with the present invention.

With reference to FIG. 2, the foregoing method is implemented with a system comprising a computer (10), a digital imaging device (20), a digital probe device (40) and an automatic, electronic acupuncture device (30). The digital probe device (40) is connected to the computer (10). The computer (10) has an acupuncture medical treatment database (11) including prescriptions for vital acupuncture points associated with specific diseases. Each prescription identifies which acupuncture points can be used to cure specific diseases.

The computer (10) uses the digital imaging device (20) to take a picture of a patient's body. The digital imaging device (20) is a digital still camera, digital video camera, etc.

The computer (10) adjusts the size of the part of the picture of the patient's body containing the vital acupuncture point of interest to the size of the standard picture in computer memory on which all vital acupuncture points are marked.

The computer (10) is used to locate locates acupuncture points on the picture of the person by overlaying the standard picture over the adjusted picture of the patient's body to find the approximate locations of the vital acupuncture points on the patient's picture. Then the digital probe device (40) is used to touch the patient's skin where a vital acupuncture point is located according to the patient's picture in the computer (10). With the digital probe at the approximate location of the desired vital acupuncture point, the digital probe device (40) outputs a fixed current signal to the skin and receives a voltage feedback signal to calculate resistance of the location. Since resistance of the skin at a vital acupuncture point differs from the resistance of the other skin at other locations, the digital probe device can be used to determine the exact location of the vital acupuncture point. Therefore, the computer can amend the positions of the vital acupuncture points on the patient's picture.

The computer marks the vital acupuncture points on the patient's picture based on prescriptions in the acupuncture medical treatment database (11). The acupuncture medical treatment database (11) has the prescriptions for any kind disease so a practitioner can select a suitable prescription including acupuncture points for the present disease to mark the acupuncture points on the patient's picture shown on the computer.

The computer controls the electronic acupuncture device and causes it to output an electric signal to the appropriate vital acupuncture points on the patient's body based on the patient's picture on the computer.

The computer and the digital probe device (40) can be used to find the correct locations of the appropriate vital acupuncture points and show the suitable acupuncture points for a specific disease. Therefore, the computer (10) and the digital probe device (40) also can be used to instruct students in finding the vital acupuncture points.

Figure 3:
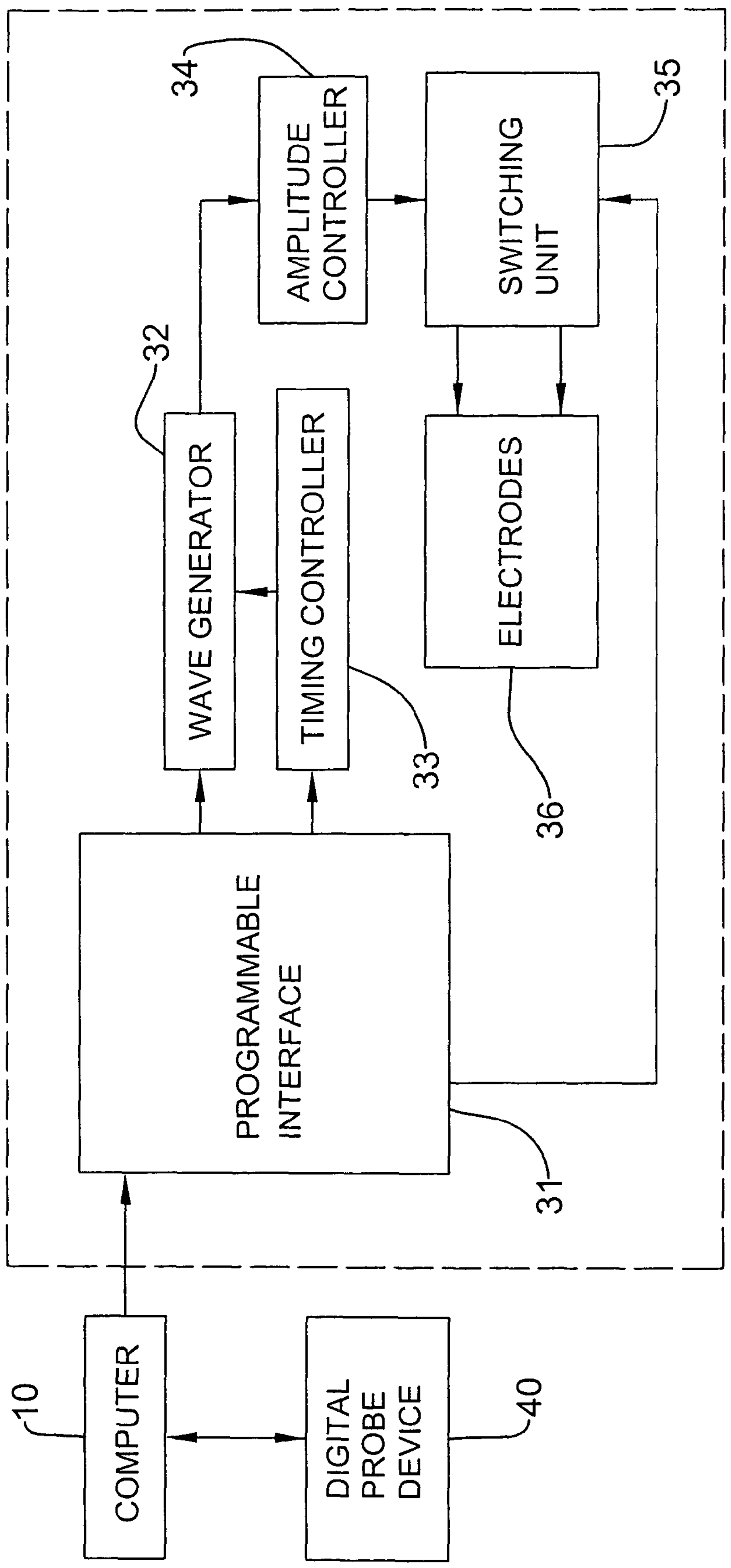
FIG. 3 is a functional block diagram of the electronic acupuncture device in FIG. 2.

With reference to FIG. 3, the forgoing electronic acupuncture device (30) includes a programmable interface (31), a wave generator (32), a timing controller (33), an amplitude controller (34), a switching unit (35) and multiple electrodes (36).

The programmable interface (31) is connected to the computer (10) to receive a signal from the digital probe device (40) or to send out the stimulating wave signal from the computer (10).

The wave generator (32) has an adjustable duty cycle, outputs a stimulative wave signal with an adjustable amplitude and is connected to the programmable interface (31) and the timing controller (33). The timing controller (33) adjusts the duty cycle of the wave generator (32). Therefore the wave generator (32) outputs different stimulative wave signals.

The amplitude controller (34) is connected to the wave generator (32) to control the amplitude of the stimulative wave signal from the wave generator (32).

The switching unit (35) is connected to the programmable interface (31), the amplitude controller (34) and the electrodes (36). The computer (10) controls the switching unit (35) through the programmable interface (31) to select a specific electrode (36) connected to the amplitude controller (34). Each electrode is used to touch the skin of the body of the patient. The electrode (36) can be a flat pad or a pointed needle.

The computer (10) displays the patient's picture with the vital acupuncture points to the practitioner. The practitioner can use the electrodes to place the acupuncture points on the skin based on the patient's picture. Therefore the practitioner can be more medically efficient.

Based on the forgoing description, the present invention can be easily and correctly finding vital acupuncture points. Therefore, the practitioner can place the electrodes at the correct locations of the vital acupuncture points for a good curative effect.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A computer-aided automatic vital acupuncture point alignment and electronic acupuncture method, comprising (a) taking a picture of a patient's body;

(b) adjusting the patient's picture to the same size as a standard body's picture with vital acupuncture points;

(c) locating vital acupuncture points on the patient's picture by overlaying the standard picture on the patient's picture;

(d) localizing the vital acupuncture points on the patient's body with a digital probe device;

(e) marking vital acupuncture points to treat the patient's disease on the patient's picture based on prescriptions to treat the patient's disease;

(f) applying an acupuncture electrode to the appropriate vital acupuncture point on the patient's body based on the patient's picture; and (g) outputting an electrical signal to the vital acupuncture points.

2. The method as claimed in claim 1, wherein step (b) further adjusts parts of the patient's picture to the same size as corresponding parts of the standard body's picture.

3. A computer-aided automatic vital acupuncture point alignment and electronic acupuncture system, comprising:

a computer having a acupuncture medical treatment database with acupuncture prescriptions to treat diseases, wherein each prescription identifies specific acupuncture points to treat specific diseases;

a digital imaging device connected to the computer to take a picture of patient's body;

a digital probe device connected to the computer to localize vital acupuncture points by detecting skin resistance; and an electronic acupuncture device connected to the computer to output different electronic wave signals with different amplitudes.

4. The system as clamed in claim 3, wherein the electronic acupuncture device further comprises:

a programmable interface connected to the computer;

a wave generator connected to the programmable interface;

a timing controller connected to the programmable interface and the wave generator;

an amplitude controller connected to the wave generator to control the amplitude of the electronic wave signal;

multiple electrodes connected to the amplitude controller through a switching unit to touch vital acupuncture points on the skin, where the switching unit connects a specific electrode to the amplitude controller.

5. The system as claimed in claim 4, wherein the programmable interface further is connected to and controls the switching unit to connect the specific electrode to the amplitude controller.

6. The system as claimed in claim 4, wherein each electrode is a flat pad.

7. The system as claimed in claim 4, wherein each electrode is a pointed needle.

* * * * *